(12) United States Patent
Gilevich et al.

(10) Patent No.: US 7,453,980 B1
(45) Date of Patent: Nov. 18, 2008

(54) APPARATUS AND METHOD FOR ACQUIRING AN IMAGE OF AN OBJECT

(76) Inventors: Alexander I. Gilevich, 821 Springfield Ter., Sunnyvale, CA (US) 94087; Brian R. Higgins, 4328 Lorren Dr., Fremont, CA (US) 94536

( * ) Notice: Subject to any disclaimer, the term of this patent is extended or adjusted under 35 U.S.C. 154(b) by 0 days.

(21) Appl. No.: 11/823,069

(22) Filed: Jun. 25, 2007

(51) Int. Cl.
*G01N 23/04* (2006.01)

(52) U.S. Cl. .......................................... 378/57; 378/62

(58) Field of Classification Search ................... 378/57, 378/4, 208, 205, 62, 95
See application file for complete search history.

(56) References Cited

U.S. PATENT DOCUMENTS

| | | | |
|---|---|---|---|
| 4,984,002 A | 1/1991 | Kokubo | |
| 5,864,600 A * | 1/1999 | Gray et al. | 378/57 |
| 6,005,618 A | 12/1999 | Fukui et al. | |
| 6,603,512 B2 | 8/2003 | Shimokawa | |
| 6,765,619 B1 | 7/2004 | Deng et al. | |
| 6,872,001 B1 | 3/2005 | Gilevich | |
| 7,012,987 B1 | 3/2006 | Annis | |
| 2003/0090582 A1 | 5/2003 | Shimokawa | |

\* cited by examiner

*Primary Examiner*—Hoon Song
(74) *Attorney, Agent, or Firm*—Mark A. Bauman

(57) ABSTRACT

The present invention is an apparatus and method for acquiring an image of an object and its contents from a stream of objects as they are transported by a conveyor. The image of the object is acquired by projecting a beam of electromagnetic radiation through the object and converting the resultant electromagnetic radiation by a sensor. The sensor accumulates the resultant electromagnetic radiation over a period of time that is a pre-defined relationship or function of the spatial relationship between the position of the object and the beam of electromagnetic radiation. A setup means is provided which allows a user to pre-define a set of constants in the pre-defined relationship.

19 Claims, 5 Drawing Sheets

APPARATUS AND METHOD FOR ACQUIRING AN IMAGE OF AN OBJECT

TECHNICAL FIELD

The present invention relates in general to producing an image of an object and more specifically to a method and apparatus for optimizing the contrast of an image to facilitate inspection of an article.

BACKGROUND OF THE INVENTION

The prior art is replete with scores of patents which describe image acquisition systems. Such systems are useful for acquiring and producing images of a variety of objects for varied applications.

In these systems, various types of electromagnetic radiation are used to illuminate or interrogate an object. One type of image acquisition system utilizes electronic circuitry to obtain, process, and produce an image of an object or article.

In these electronic systems, an image sensor is often utilized to receive reflected or refracted electromagnetic radiation from the object. Alternatively, the image sensor may receive transmitted electromagnetic radiation that has passed through the object.

Often, the image sensor is connected to a controller which is configured to receive signals produced by the image sensor and to provide control signals which control the rate of image acquisition and signal transfer.

Some types of objects or articles are difficult to interrogate by image acquisition systems when the electromagnetic radiation is received by the image sensor having passed through the object or article. When the electromagnetic radiation travels along a path through the object or article under interrogation, the resulting electromagnetic radiation that exits the object and is received by the image sensor is often a function of the density of the object along the path of travel of the electromagnetic radiation.

An especially challenging object or article for interrogation is a cylindrical container such as a bottle, can, or jar. In this situation, the path length of the electromagnetic radiation through the object or material varies significantly depending on the spatial position of the container relative to the beam of electromagnetic radiation. For example, in bottles containing low density fluid, the density along a path of travel through an edge of the container can be significantly greater than the density encountered along a path of travel through a mid region of the bottle because the density of the container walls can significantly attenuate the electromagnetic radiation. Alternatively, in a thin walled container containing a dense fluid, the density along the path of travel through a mid region of the bottle can be significantly greater than the density encountered along the path of travel through an edge of the container.

These various density paths present challenges to the image sensor due to the finite dynamic range of the sensor. The relative merit of the interrogation of the image acquisition system begins to degrade as the difference in the density paths approaches the dynamic range of the sensor. The relative merit or performance of the image acquisition system becomes especially poor when the difference in path density exceeds the dynamic range of the sensor.

This degradation of relative merit or performance decreases the effectiveness of the interrogation of the object or article, effectively blocking or blinding certain portions of the object or article.

In the production of food articles, desired comestible products are introduced into containers such as bottles or cans for preservation and delivery to a consumer. Occasionally, undesirable foreign objects are also introduced into the containers during the process of manufacture. These undesirable foreign objects have the potential of producing discomfort or harm to the consumer. For this reason, image acquisition systems employing electromagnetic radiation to travel along a plurality of paths through the container to effectively interrogate the object are employed by manufacturers to identify containers containing undesirable foreign objects before they reach the consumer. Often, x-ray radiation is chosen in these applications as the form of electromagnetic radiation due to its superior characteristics. An exemplary example of such an image acquisition system is illustrated and discussed in the U.S. Pat. No. 6,872,001 and incorporated herein.

The merit or effectiveness of the interrogation is especially important in this example since this has a direct bearing on the overall percentage or ratio of containers having foreign material that are caught or intercepted before reaching the consumer. Unfortunately, the characteristics of the containers or objects themselves can vary significantly from object to object and lot to lot which can confound the interrogation process resulting in erroneous information. This erroneous information can cause loss of productivity in the case of false rejections or loss of quality in the case of false acceptance.

So, what is needed is an apparatus and method for acquiring an image of an object to effectively inspect an object that is not prone or vulnerable to substantial blocking or blinding of certain portions of the object due to variations in the density of the path of travel of the electromagnetic radiation through the object.

SUMMARY OF THE INVENTION

A first aspect of the present invention is to provide an apparatus for acquiring an image of an object in a stream of objects, which includes an emitter operable to produce and direct a beam of electromagnetic radiation; and a conveyor configured to transport the object through the beam of electromagnetic radiation; and a sensor positioned in receiving relation to a portion of the beam of electromagnetic radiation that passed through the object, and operable to provide a signal in response to the accumulated received portion of the beam of electromagnetic radiation over an integration time interval; and a controller connected in signal receiving and command transmitting relation to the sensor, and configured to specify the integration time interval as a function of the relative position of the object in relation to the beam of electromagnetic radiation, and operable to provide image data derived from a plurality of the signals; and an image memory circuit connected to the controller and operable to receive the image data, and operable to store the image data in an image format.

Another aspect of the present invention includes an emitting means operable to project a beam of electromagnetic radiation; and a transport means configured to move the object in intersecting relation to the beam of electromagnetic radiation; and a sensing means positioned in receiving relation to a portion of the beam of electromagnetic radiation, and operable to provide a signal representative of the received electromagnetic radiation accumulated over a controlled time interval in response to a request; and a controlling means connected in transmission relation to the sensor, and operable to provide the request to transmit the signal to the controller, and further operable to gather a plurality of the signals and assemble the signals together to form an image representing the object, and wherein the controller is operable to specify the time interval in relation to a relative position of the object to the beam of electromagnetic radiation.

Still further, another aspect of the invention includes a method for acquiring an image of an object in a stream of objects, which includes providing a beam of electromagnetic radiation; and transporting the object through the beam of electromagnetic radiation; and sensing a portion of the beam of electromagnetic radiation that passed through the object; and computing a time interval that is a function of the relative position of the object in relation to the beam of electromagnetic radiation; and generating a signal by accumulating the sensed portion of the beam of electromagnetic radiation over the computed time interval; and assembling the image of the object by organizing a plurality of the signals as the object is transported through the beam of electromagnetic radiation.

These and other aspects of the present invention will be discussed in greater detail hereinafter.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
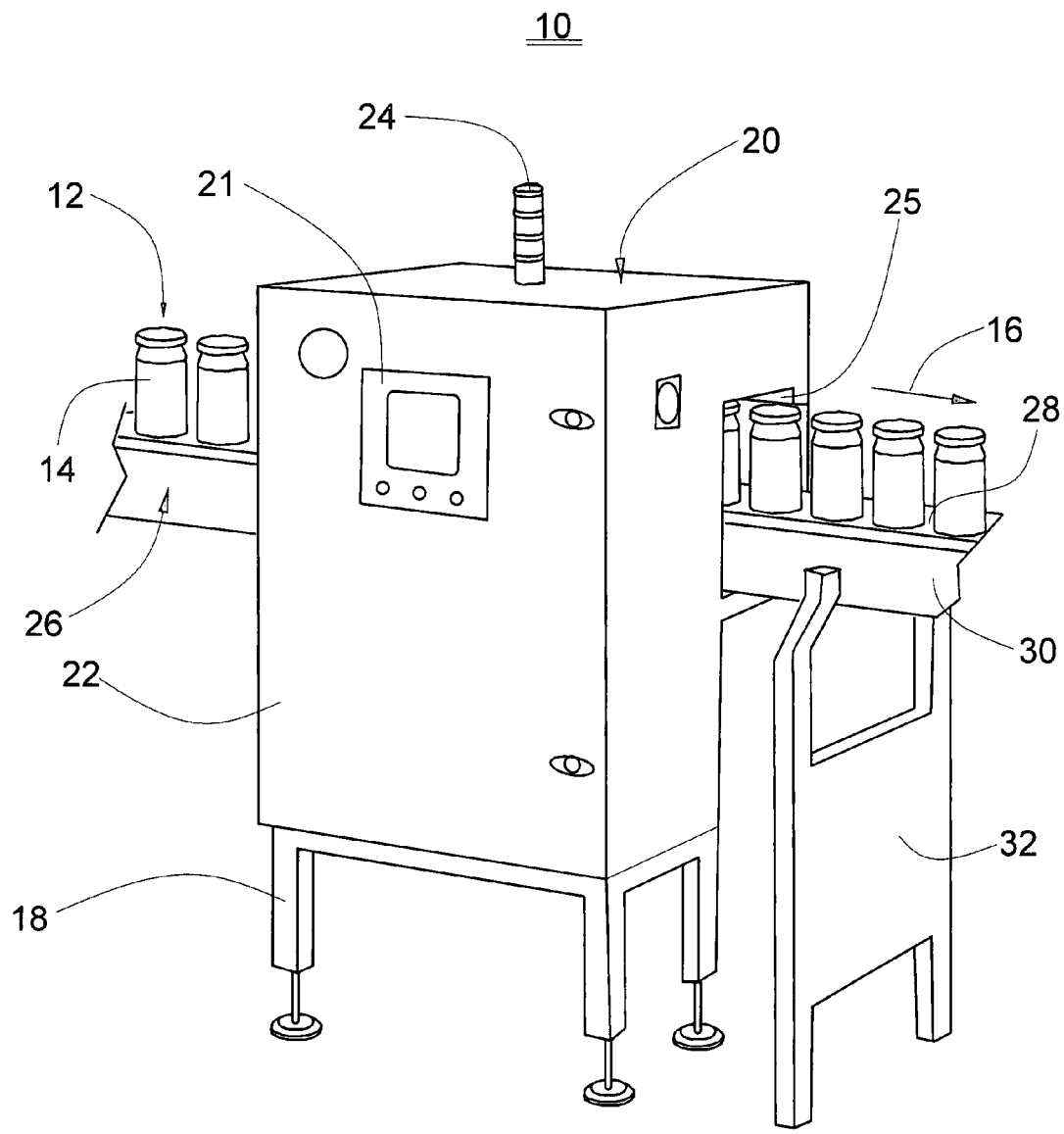
FIG. 1 is an isometric view of the image acquisition system in an interrogating configuration of a stream of objects.

A preferred embodiment of an apparatus for acquiring an image 10 is shown in FIG. 1. The apparatus 10 is positioned in transmission relation to a stream of objects 12 in which individual objects 14 are interrogated by the apparatus 10. Objects 14 in the stream of objects 12 may include, but is not limited to objects or containers including jars, bottles, or cans having varied composition and containing a variety of contents. The objects 14 or containers range in height from 15 mm to 220 mm and from a diameter of 20 mm to 180 mm. Each object 14 or container has an outer shell or wall enclosing a volume which is operable to hold a comestible or other liquid or mixture. The outer shell or wall may have a thickness on the order of 2.5 mm. However, the outer shell or wall is known in the art to vary greatly. Each object 14 is interrogated by the apparatus of acquiring an image 10 to determine if undesirable ingredients or foreign material are present in the object 14. This undesirable material may include but is not limited to shards of glass, metal fragments, stones, rubber pieces, hard plastic, or bones. The apparatus for acquiring an image 10 interrogates the objects with x-ray radiation to ascertain the presence of the undesirable ingredients or foreign material. X-ray radiation is known in the art to penetrate through the objects 14 to reveal characteristics of the enclosed contents as it responds and interacts with the objects 14 and the contents enclosed in the objects.

The objects 14 are transported along a path through the apparatus for acquiring an image 10 in a direction generally represented by the arrow 16 at a speed. This speed has a range and the range extends from a low value of 2 meters per minute to a high value of 250 meters per minute.

The apparatus for acquiring an image 10 is mounted on a platform 18 suitable for mounting to a floor (not shown) or other suitable mounting structure. The apparatus 10 includes an enclosure 20 suitable for housing and protecting sensitive components needed for the proper operation of the apparatus 10 by a user (not shown). The enclosure 20 has an access door 22 which may be opened during maintenance to service various components of the apparatus 10. A user interface 21 is mounted on the access door 22. A signal light 24 is mounted to the enclosure 20 to provide an operational indication to the user of the status of the apparatus 10.

The stream of objects 12 are transported through an aperture 25 in the apparatus 10 on a transport means or conveyor 26. The conveyor 26 includes a belt 28 configured to support the objects 14 along a path of travel. The belt 28 is supported and guided by a conveyor frame 30. The conveyor frame 30 is mounted to a support 32 which is positioned on the floor or other suitable support structure.

Figure 2:
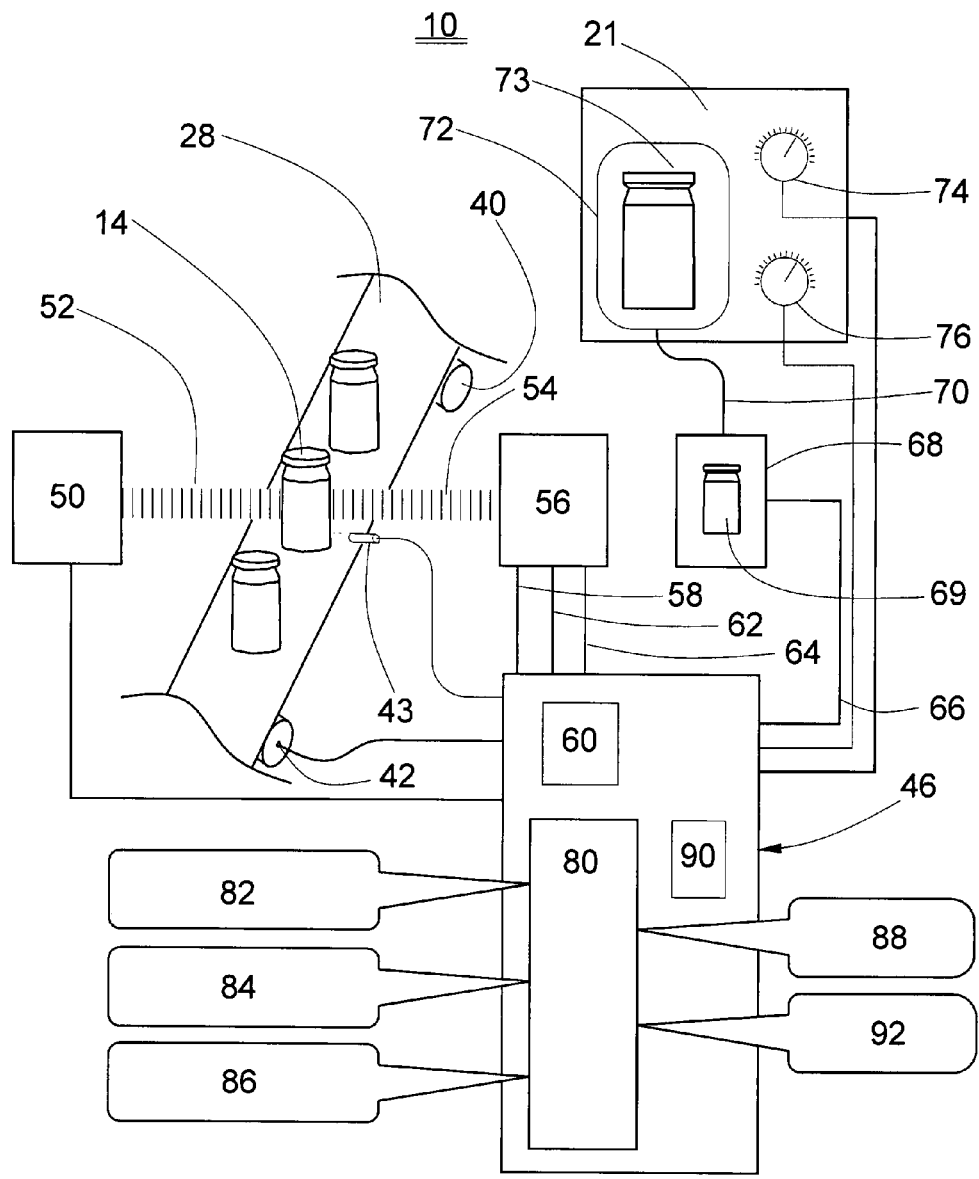
FIG. 2 is a system block diagram of the image acquisition system.

Referring now to FIG. 2, the apparatus for acquiring an image 10 includes the belt 28 configured to transport the objects 14 through the aperture 25 (FIG. 1). The conveyor frame 30 (FIG. 1) supports a plurality of pulleys 40 suitable to engage the belt 28 along its path of travel. A timing or index sensor 42 is operationally tied to one of the pulleys 40 and configured to provide an index pulse representative of a belt 28 distance of travel. The index pulse travels along an index pulse cable from the index sensor 42 to a controller 46 whose elements and operation will be discussed in further details below.

A body trigger sensor 43 is mounted in sensing relation to the objects 14 as they are transported on the belt 28 through the beam of electromagnetic radiation 52. The body trigger sensor 43 is positioned so that a leading edge of the object 14 provides a trigger signal that is sent to the controller 46 whose operation will be discussed in further detail below. The body trigger sensor 43 is an optical proximity switch, although other types of sensors known in the art could be used in this application without departing from the scope of this invention.

An emitter 50 is arranged in a manner to transmit a beam of electromagnetic radiation 52 across the aperture 25 (FIG. 1) in intersecting relation to the stream of objects 12 (FIG. 1). Periodically, one of the objects 14 in the stream objects 12 (FIG. 1) intersects the beam of electromagnetic radiation 52. In this situation, the beam of electromagnetic radiation 52 will interact with the object 14 in an interrogating manner, with some of the energy being defracted, refracted, reflected, or absorbed. In a preferred embodiment, the emitter 50 is an x-ray source having a spectral range of 20 to 70 kV. The interaction of the beam 52 and the object 14 can reveal aspects or characteristics of the object 14 as will be discussed in further detail below.

Electromagnetic radiation that has traveled beyond the stream of objects is referred to as a portion of the beam of electromagnetic radiation, and is generally designated by the numeral 54. The portion 54 is received by a sensor 56. The sensor 56 is selected to be effective to convert the portion 54 to an electrical signal. In a preferred embodiment, the sensor 56 is a linear diode array in which a time of integration is adjustable and is further substantially independent from a line readout rate as will be discussed in further detail below. In one embodiment, the sensor 56 is composed of a plurality of linear diode arrays arranged in linear fashion to provide sufficient resolution for imaging the objects 14. Each linear diode array in the sensor 56 has 128 individual elements whose respective voltage level can be read using methods that are well known in the art. One skilled in the art would further recognize that the sensor 56 could also be an area array sensor.

The sensor 56 provides a sensor signal 58 which is representative of the portion of the beam of electromagnetic radiation 54 which is received on each individual pixel. The received portion for a given integration time on each individual sensor signal 58 is time multiplexed in serial fashion according to various control signals which will be discussed in further detail below. The sensor signal 58 is sent to the controller 46 where it is amplified, normalized, correlated double sampled, and converted to digital image data in a video processor 60 located in the controller 46. The video processor 60 provides a suite of control signals to manage the operation of the sensor 56. These control signals include a line clock 62 and a request or reset signal 64. The line clock 62 instructs the sensor 56 to read out individual pixels to develop the sensor signal 58 and is synchronized with the correlated double sampler and analog to digital converters located in the video processor 60. The request or reset signal 64 is provided by the controller 46 and effectively controls the time of integration of the sensor 62 which makes it possible to vary the amplitude of signal that will result for a given amount of electromagnetic radiation that is received by the sensor 62. Careful manipulation of the request or reset signal 64 relative to other control signals provided to the sensor 56 has been found to be especially advantageous. For example, the sensor 56 has a limited dynamic range, and is prone to saturation when the received portion of the beam of electromagnetic radiation 54 is accumulated to a point that it exceeds its sensing capabilities. The request or reset signal 64 is coordinated to reduce the amount of accumulation or integration time afforded to the sensor, thus reducing its vulnerability to experiencing a saturated condition and effectively increasing its dynamic range. Operation of the control aspects of the request or reset signal 64 will be discussed in further detail below.

Image data provided by the video processor 60 is transmitted along the image data bus 66 to an image memory 68. The image memory 68 is operable to provide an image 69 presented as video data through a video bus 70. The video data provided by the video bus 70 is formatted in a manner to be shown as an image 73 on a display screen 72.

The display 72 is part of the user interface 21. The user interface also includes a first image control 74 and a second image control 76. The first and second image controls 74 and 76 are operably connected to the controller 46 and utilized by the user (not shown) during a setup process to enhance the contrast of the image 73 of the object 14 on the display screen 72, and will be described in more detail below. The first and second image controls 74 and 76 are panel mounted rotary potentiometers, although other forms of input devices may be used without departing from the scope of this invention including, but not limited to, encoders, linear potentiometers, discrete switches, and virtual widgets or icons displayed on the display screen 72 in combination with a touch screen (not shown).

The controller 46 includes a program memory 80 which contains program code or instructions specifying various operational aspects of the apparatus for acquiring an image 10. The program memory 80 includes an edge detection routine 82 operable to provide a designation to other routines operating within the controller 46 of the presence of a leading edge of the object 14. The edge detection routine 82 receives input from the body trigger sensor 43 whose operation is discussed above. However, one skilled in the art would recognize that the edge detection routine 82 could provide similar operation by processing data provided by the video processor 60 which could similarly provide indication of a passing object 14.

A tracking routine 84 is included in the program memory 80 and is operational to provide an indication to the controller 46 of the relative location of the object 14 relative to the beam of electromagnetic radiation 52. The tracking routine 84 receives information from the edge detection routine 82 as well as the timing index sensor 42 to calculate the current relative location of the object 14 as discussed above.

An integration time control routine 86 resides in the program memory 80. The integration time control routine 86 is operational to control the request or reset signal line 64 from the controller 46 to the sensor 56 to specify or dictate the amount of time that the sensor 56 accumulates or integrates the received portion of the beam of electromagnetic radiation 54 which directly impacts the transfer function which provides elements of the sensor signal 58 provided by the sensor 56.

The program memory 80 also includes a parameter setup routine 88 which orchestrates the operation and guides the user through a configuration process to compute parameters which are used to optimize the image 69 for contrast to improve the ability of the controller 46 to interrogate the object 14 to reveal the presence of undesirable or foreign matter which may be contained in the object 14. The results of the parameter setup routine 88 are stored in a parameter memory 90.

The program memory 80 further includes a parameter selection routine 92 which is operational to provide the integration control routine 86 with the appropriate information to the control the integration time for the sensor 56. The parameter selection routine 92 acquires the information to control the integration time by transforming the current relative location of the object 14 provided by the tracking routine 82 and the information contained in the parameter memory 90. The parameter selection routine 92 includes a one dimensional look up table having rows which are indexed to the relative location of the object 14 holding values equal to the appropriate integration time for the sensor 56.

Figure 3:
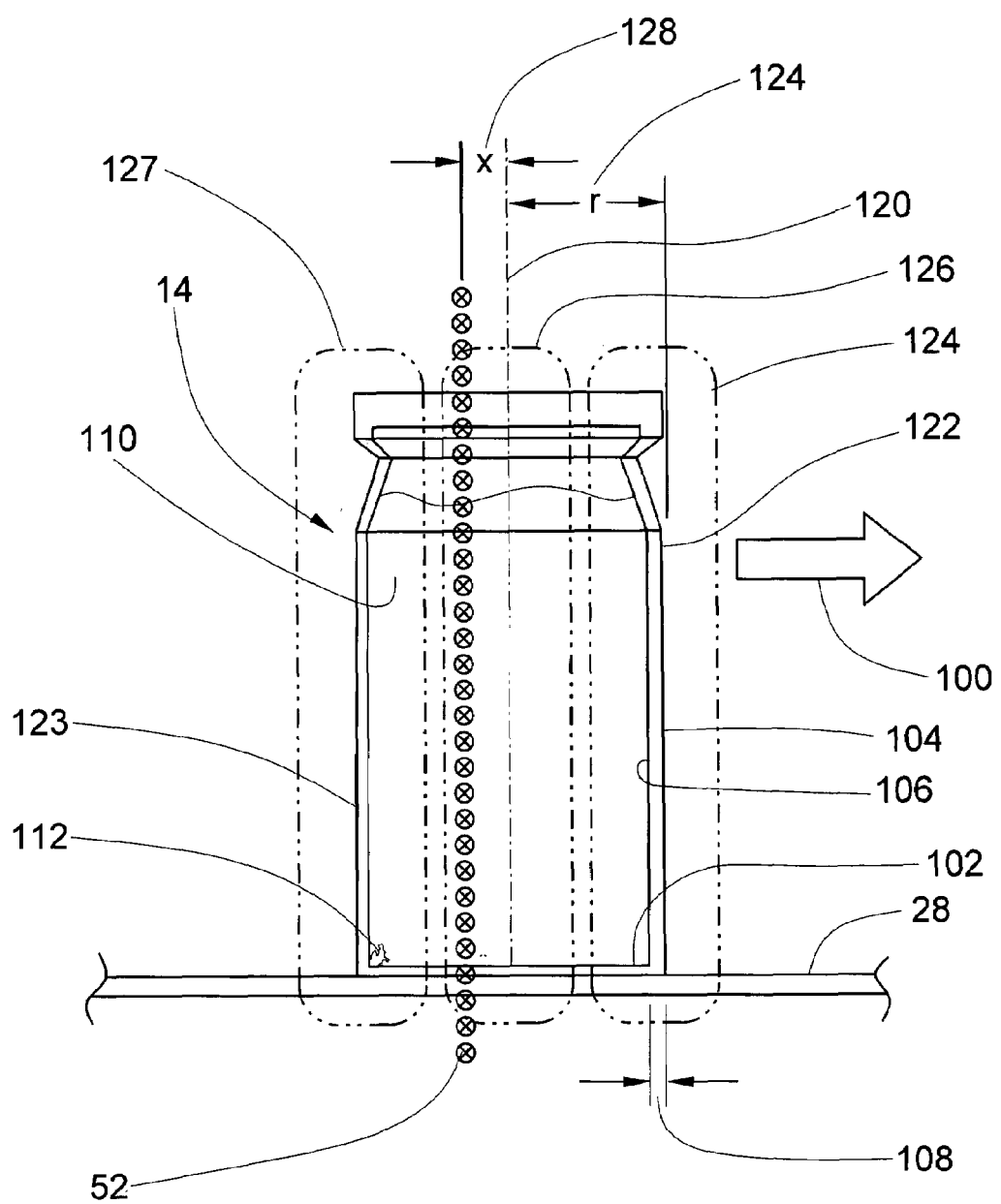
FIG. 3 is an elevation view of an object being interrogated by a beam of electromagnetic radiation while being transported by a conveyor.

Referring now to FIG. 3, the beam of electromagnetic radiation 52 intersects or penetrates the object 14 as it travels in a direction generally indicated by the arrow 100. The object 14 is a container having a base 102, an outer enclosing surface 104, and an inner surface 106. The base 102 of the object 14 is in contact, and is transported by the belt 28 through the beam of electromagnetic radiation 52. The object 14 holds a substance 110 contained therein which may contain foreign or undesirable material 112. It is desirable that the apparatus for acquiring an image 10 be adept and capable of providing an image of the foreign or undesirable material 112 contained in the object 14 to allow a user or downstream operation to remove the offending object 14 before it reaches a consumer.

The distance between the outer enclosing surface 104 and the inner surface 106 forms a wall having a thickness 108. The wall of the object 14 is plastic, glass, tin, aluminum, or any other material known in the art to be useful for the containment of the substance 100. The wall thickness 108 is known in the art to have a variance which can confound or otherwise complicate the process of determining or interrogating the object 14 to locate the presence of the foreign or undesirable material 112.

The object 14 has a longitudinal axis 120 as depicted in the figure. A radius measurement "r" generally depicted by the numeral 124 extends from the longitudinal axis 120 to a leading edge or extent 122 of the object 14. A region associated with this leading edge or extent 122 is designated as a leading region 124. Another region associated the longitudinal axis 120 is designated as a middle region 126. Another region located opposite from the leading region 124 is the trailing region 127. The object 14 has a trailing edge or extent 123 which is associated with the trailing region 127.

A reference distance measured between the longitudinal axis 120 and a projection of the beam of electromagnetic radiation 52 represents a scalar tracked position "x" and is generally represented by the numeral 128. The tracked position "x" 128 has a value of zero when the beam of electromagnetic radiation 52 is coincident with the longitudinal axis 120. The tracked position "x" 128 has a value equal to the radius 124 when the beam of electromagnetic radiation 52 is coincident with either the leading edge or extent 122 or the trailing edge or extent 123.

Figure 4:
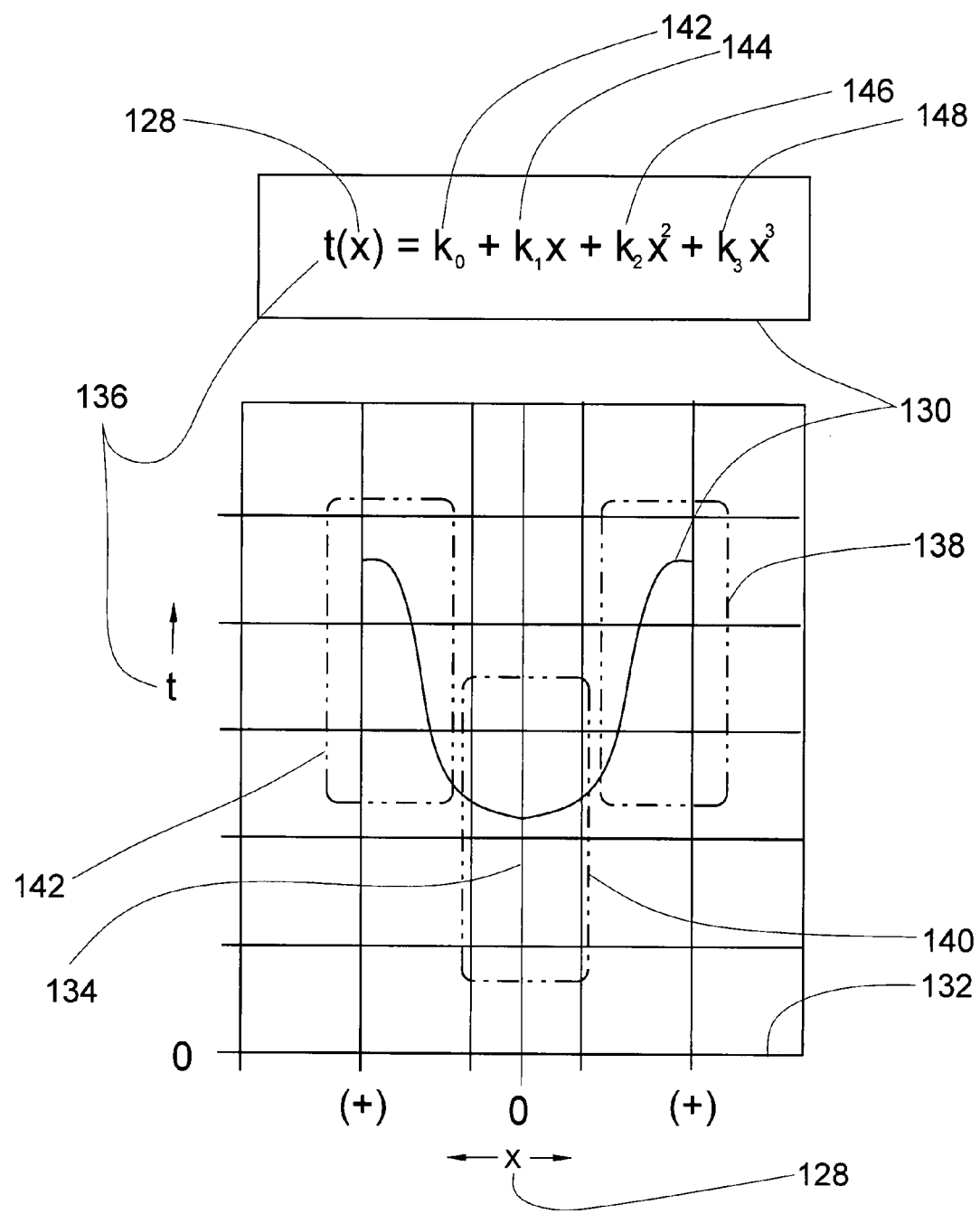
FIG. 4 is a graphical representation of an example of the mathematical relationship between the tracked position and the integration time of the sensor.

Referring now to FIG. 4, an integration time relationship 130 is illustrated as a function of the scalar tracked position 128. The integration time relationship 130 is defined by the parameter setup routine 88 (FIG. 2), and is implemented in the parameter selection routine 92 (FIG. 2) during operation of the apparatus for acquiring an image 10. The scalar tracked position "x" 128 is plotted on the scalar positive horizontal axis 132. A vertical axis 134 is depicted perpendicular to the horizontal axis 132. The vertical axis 134 represents a measure of integration time "t" 136.

For purposes of illustration, a first boundary 138 corresponds to the scalar tracked position "x" 128 of the leading region 124 (FIG. 3). A second boundary 140 corresponds to the scalar tracked position "x" 128 of the middle region 126 (FIG. 3). A third boundary 142 corresponds to the scalar tracked position "x" 128 of the trailing region 127 (FIG. 3). From inspection of the figure, it is evident that the integration time 136 is at its highest level or value within the first boundary 138 and third boundary 142. Further from inspection of the figure, it is evident that the integration time 136 is at its lowest level or value within the second boundary 140.

The integration timer relationship 130 is also illustrated mathematically in FIG. 4. Here, the integration time 136 is shown as the sum of an offset constant 142; and the product of the scalar tracked position "x" 128 and a first order constant 144; and the product of the square of the scalar tracked position "x" 128 and a second order constant 146; and the product of the cube of the scalar tracked position "x" 128 and a third order constant 148. One skilled in the art would recognize that there are other functions or relationships which could be used to accomplish a similar result.

Figure 5:
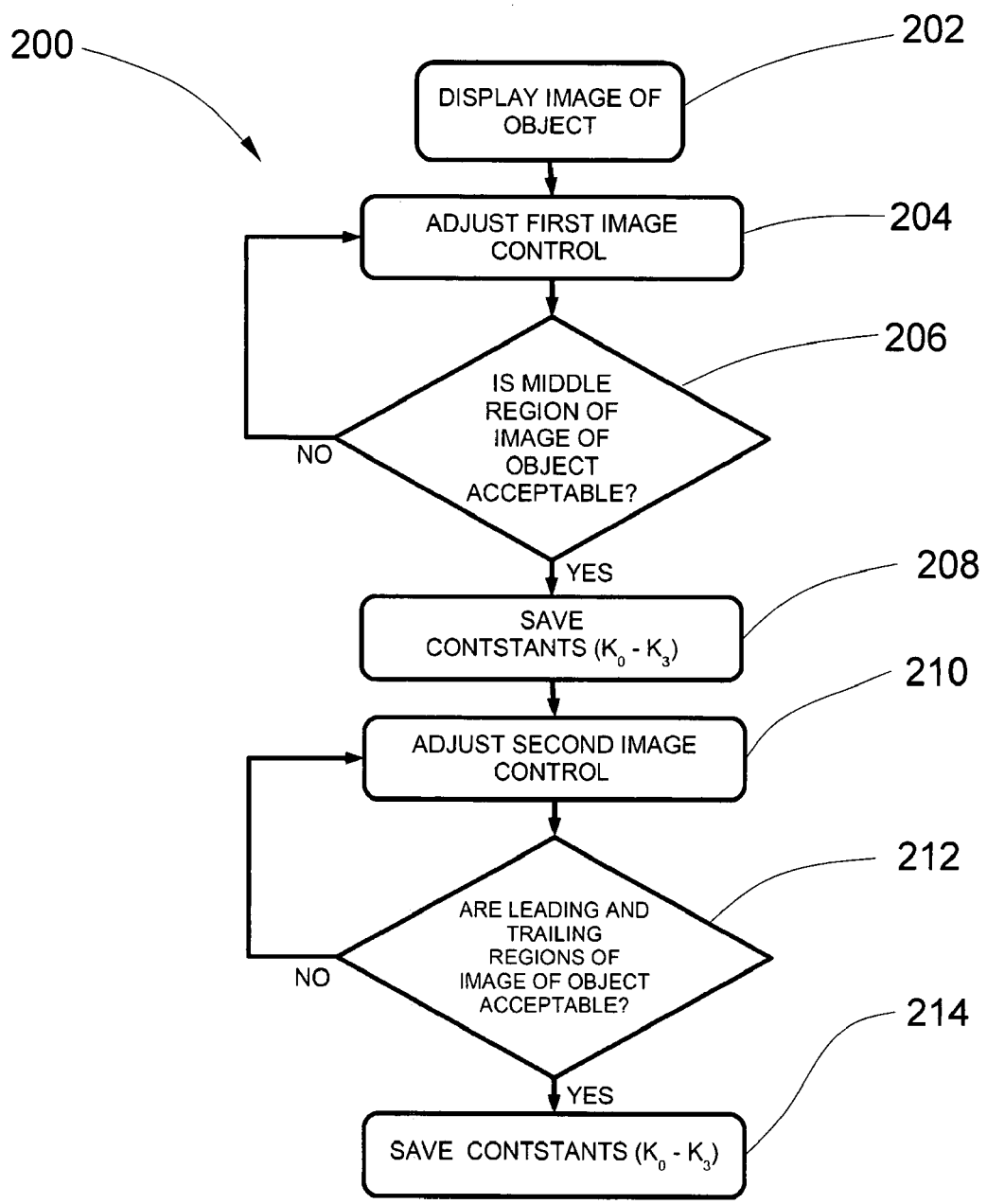
FIG. 5 is a process chart of the steps to determine the pre-defined constants.

Referring now to FIGS. 2 and 5, the parameter setup routine 88 (FIG. 2) includes a set of ordered processes which are summarized and generally indicated by the numeral 200. Each object 14 from the stream of objects 12 (FIG. 1) is displayed as an image 73 on the display screen 72 as they are transported through the aperture 25 as depicted by the symbol generally indicated by the numeral 202. The user (not shown) while viewing subsequent images of the objects 14 on the display screen 72 adjusts or otherwise modifies the setting of the first image control 74 as depicted in the process step 204. During this sequence, the user examines the middle region 126 (FIG. 3) of the image of the object 14 to determine if the image is acceptable as depicted in the process step 206. If the image of the object 14 in the middle region 126 (FIG. 3) is too dark, then the user may adjust the first image control 74 to increase the effective integration time during this portion of the imaging routine to accumulate for a longer period of time. Conversely, if the image of the object 14 in the middle region 126 (FIG. 3) is too light, then the user may adjust the first image control 74 to decrease the effective integration time during this portion of the imaging routine to accumulate for a shorter period of time. The emission voltage and current exposure may also be adjusted by the operator during this sequence.

Once the user is satisfied with the image of the object 14 in the middle region 126 (FIG. 3), the controller 46 saves the constants as depicted in the process step 208.

Next, the user while viewing subsequent images of the objects 14 on the display screen 72 adjusts or otherwise modifies the setting of the second image control 76 as depicted in the process step 210. During this sequence, the user examines the leading region 124 (FIG. 3) and trailing region 127 (FIG. 3) of the image of the object 14 to determine if the image is acceptable as depicted in the process step 212. If the image of the object 14 in the leading region 124 (FIG. 3) or the trailing region 127 (FIG. 3) is too light or bright, then the user may adjust the second image control 76 to decrease the effective integration time during this portion of the imaging routine to accumulate for a shorter period of time to provide a darker image.

Once the user is satisfied with the image of the object 14 in the leading region 124 (FIG. 3) and trailing region 127 (FIG. 3), the controller 46 saves the constants as depicted in the process step 214.

Operation

The operation of the present invention is believed to be readily apparent and is briefly summarized in the paragraphs which follow.

In operation, the apparatus for acquiring an image 10 provides or emits a beam of electromagnetic radiation 52 from the emitter 50 through an object 14 contained in a stream of objects 12. The object 14 is transported through the beam of electromagnetic radiation 52 by the conveyor or transport means 26 as it rests on the belt 28. A portion of the beam of electromagnetic radiation 54 that passed through the object 14 is sensed or converted by the sensor 56 and accumulated on the sensor 56 over a period of time which is coordinated by the request or reset signal 64 that is provide by the controller 46. A line clock 62 is provided by the controller 46 to sequence or otherwise coordinate and read out portions or pixels of the sensor 56 thereby providing the sensor signal 58. In this manner, a signal is generated by accumulating the sensed portion of the beam of electromagnetic radiation 52 over the integration time 136 interval. The integration time 136 is computed by the controller 46, and is a function of the relative position of the object 14 in relation to the beam of electromagnetic radiation 52. Specifically, the time interval is computed by detecting the leading edge 122 of the object 14 by utilizing the edge detection routine 82 as it passes through the beam of electromagnetic radiation 52, and tracking the position or scaler tracked position 128 of the object 14 relative to the beam of electromagnetic radiation 52 by utilizing the tracking routine 84, and utilizing the integration time routine 86 which calculates the time interval or integration time 136 using the pre-defined or integration time relationship 130 as stored in the parameter memory 90 and selected by the parameter selection routine 92. The integration time relationship 130 is a function of the tracked position 128 of the object 14 relative to the beam of electromagnetic radiation 52. In one embodiment, the pre-defined or integration time relationship 130 is defined as an arithmetic polynomial equation having the set of pre-defined constants 142, 144, 146, and 148.

Yet further, the controller 46 assembles the image 73 of the object 14 by organizing a plurality readings of the sensor signal 58 as the object 14 is transported through the beam of electromagnetic radiation 52. The image of the object 73 is displayed on the display screen 72.

The pre-defined constants are defined by a process that includes displaying the image 73 of the object 14 to an operator or user as it is transported through the beam of electromagnetic radiation 52. The first image setting or control 74 is provided and is operable to provide input data to the controller 46. From this input data, the controller maps or transforms this data to load the pre-defined constants which include the offset constant 142, first order constant 144, second order constant 146, and third order constant 148. At the same time, images 73 of individual objects 14 are displayed on the user interface 21 as they are transported by the conveyor or transport means 26. Changes made by the user which impact the pre-defined constants are reflected in the images 73 of the individual objects 14. The user adjusts this first image setting or control 74 until the image 73 in the display 72 of the middle region 126 of the image 73 of the object 14 is satisfactory to the user. At that point, the user instructs the controller 48 via the operator interface 21 to save the predefined constants.

Then, a second image setting or control 76 is provided and is operable to determine or further refine the numerical values of the pre-defined constants which include the offset constant 142, first order constant 144, second order constant 146, and third order constant 148. At the same time, images 73 of individual objects 14 are displayed on the user interface 21 as they are transported by the conveyor or transport means 26. Changes made by the user which impact the pre-defined constants are reflected in the images 73 of the individual objects 14. The user adjusts the second image setting or control 76 until the display of the leading and trailing edges of the image 73 of the object 14 is satisfactory to the user. Then, the pre-defined constants are saved. In this manner, the user can effectively adjust or tune the system for a desired level of sensitivity which provides enhanced contrast for identifying foreign material that might be contained in within the object 14.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An apparatus for acquiring an image of an object in a stream of objects, comprising:

an emitter operable to produce and direct a beam of electromagnetic radiation;

a conveyor configured to transport the object through the beam of electromagnetic radiation;

a sensor positioned in receiving relation to a portion of the beam of electromagnetic radiation that has passed through the object, and operable to provide a signal in response to an accumulated received portion of the beam of electromagnetic radiation over an integration time interval;

a controller connected in signal receiving and command transmitting relation to the sensor, and operable to provide image data derived from a plurality of the signals;

a tracking routine configured to run on the controller and operable to provide a tracked position of the object by computing the position of the object relative to the beam of electromagnetic radiation; and an integration time control routine configured to run on the controller, and operable to specify the integration time interval based on a pre-defined relationship having pre-defined integration time constants, and wherein the pre-defined relationship is a function of the tracked position; and an image memory circuit connected to the controller and operable to receive the image data, and operable to store the image data in an image format.

2. The apparatus for acquiring an image of an object as claimed in claim 1, and wherein the object has a leading edge defined in relation to the relative motion of the object to the beam of electromagnetic radiation, and wherein the controller further comprises:

an edge detection means operable to determine when the leading edge of the object passes through the beam of electromagnetic radiation.

3. The apparatus for acquiring an image of an object as claimed in claim 2, and wherein the pre-defined relationship is defined as an arithmetic polynomial equation with pre-defined constants.

4. The apparatus for acquiring an image of an object as claimed in claim 2, and further wherein the object has a trailing edge opposite the leading edge, and a middle region located approximately halfway between the leading and the trailing edge, further comprising:

a display operable to present an image of the object from the image data as it is transported through the beam of electromagnetic radiation to a user;

a parameter setup routine configured to run on the controller;

a first image control connected in control relation to the parameter setup routine, and operable to modify the integration time constants;

a second image control connected in control relation to the parameter setup routine, and operable to modify the integration time constants;

and wherein the integration time constants are manipulated by the parameter setup routine in response to stimulus provided by the user through adjustment of the first image control in order to provide a satisfactory image of the middle region of the object, and further wherein the integration time constants are further manipulated by the parameter setup routine in response to stimulus provided by the user through adjustment of the second image control in order to provide a satisfactory image of the leading and trailing regions of the object.

5. The apparatus for acquiring an image of an object as claimed in claim 4, and wherein the beam of electromagnetic radiation is an x-ray beam.

6. The apparatus for acquiring an image of an object as claimed in claim 4, and wherein the edge detection means is a body trigger sensor.

7. The apparatus for acquiring an image of an object as claimed in claim 4, and wherein the edge detection means is a routine configured to run on the controller, and operable to query the image data stored in the image memory circuit and determine if the leading edge of the object is passing through the beam of electromagnetic radiation, and operable to trigger the controller indicating the presence of the leading edge.

8. An apparatus for acquiring an image of an object in a stream of objects, comprising:

an emitting means operable to project a beam of electromagnetic radiation;

a transport means configured to move the object in intersecting relation to the beam of electromagnetic radiation;

a sensing means positioned in receiving relation to a portion of the beam of electromagnetic radiation, and operable to provide a signal representative of the received electromagnetic radiation accumulated over a controlled time interval in response to a request; and a controlling means connected in transmission relation to the sensor, and operable to provide the request to transmit the signal to the controller, and further operable to gather a plurality of the signals and assemble the signals together to form an image representing the object, a timing means which provides a timing pulse in relation to the motion of the object provided by the transport means; and a parameter coordination means positioned in data receiving relation to the edge detection means, and positioned in pulse receiving relation to the timing means, and operable to specify the time interval for accumulation of the electromagnetic radiation from the object based on an arithmetic relationship that is a function of the data received by the edge detection means and the pulses received by the timing means.

9. The apparatus for acquiring an image of an object as claimed in claim 8, and wherein the object has a leading edge defined in relation to the relative motion of the object to the sensing means, and wherein the controlling means further comprises:

an edge detection means operable to detect the leading edge of the object as it is represented by the sensor.

10. The apparatus for acquiring an image of an object as claimed in claim 9, and wherein the arithmetic relationship is defined by a polynomial relationship having a set of pre-defined integration time constants.

11. The apparatus for acquiring an image of an object as claimed in claim 10, and wherein the pre-defined arithmetic relationship is further defined as a forth order polynomial.

12. The apparatus for acquiring an image of an object as claimed in claim 11, and wherein the image assembled by the controlling means includes an image representative of the object, and wherein the representative image of the object has a middle region, and a trailing region defined in relation to the relative motion of the object to the sensor, and wherein the apparatus further comprises:

an image display viewable by a user and configured to display the image of the object assembled by the controlling means;

a first setup screen having a first image adjustment available to a user;

a second setup screen with a second image adjustment available to a user;

and wherein the controlling means is operable to manipulate the set of integration time constants in response to the first and second image adjustments resulting in images of the objects on the image display, and wherein a user modifies the first image adjustment for satisfactory viewing of the middle region of the objects, and further wherein the user modifies the second image adjustment for satisfactory viewing of the leading and trailing regions of the objects, and wherein the pre-defined integration time constants are stored by the controlling means.

13. A method for acquiring an image of an object in a stream of objects, comprising:

providing a beam of electromagnetic radiation;

transporting the object through the beam of electromagnetic radiation;

sensing a portion of the beam of electromagnetic radiation that passed through the object;

tracking the position of the object relative to the beam of electromagnetic radiation;

computing a time interval using a pre-defined relationship of the function of the relative position of the object in relation to the beam of electromagnetic radiation;

generating a signal by accumulating the sensed portion of the beam of electromagnetic radiation over the computed time interval; and assembling the image of the object by organizing a plurality of the signals as the object is transported through the beam of electromagnetic radiation.

14. The method for acquiring an image of an object as claimed in claim 13, and wherein the object has a leading edge defined in relation to the relative motion of the object to the beam of electromagnetic radiation, and wherein the method of computing a time interval further comprises:

detecting the leading edge of the object as it passes through the beam of electromagnetic radiation.

15. The method for acquiring an image of an object as claimed in claim 14, and wherein the pre-defined relationship is defined as an arithmetic polynomial equation, further comprising:

providing a set of pre-defined constants.

16. The method for acquiring an image of an object as claimed in claim 15, and further wherein the object has a trailing edge opposite the leading edge, and a middle region located approximately halfway between the leading and the trailing edge, and wherein the method of providing the set of pre-defined constants comprises:

displaying the image of the object as it is transported through the beam of electromagnetic radiation;

providing a first image setting which is operable to determine numerical values for the pre-defined constants;

adjusting the first image setting until the display of the middle region of the image of the object is satisfactory to the user;

saving the pre-defined constants determined by the first image adjustment setting;

providing a second image setting which is operable to determine or refine the numerical values within the pre-defined constants;

adjusting the second image setting until the display of the leading and trailing edges of the image of the object is satisfactory to the user; and saving the pre-defined constants.

17. The method for acquiring an image of an object as claimed in claim 15, and wherein the pre-defined relationship is further defined as a forth order polynomial.

18. The method for acquiring an image of an object as claimed in claim 16, and wherein the pre-defined relationship is implemented as a lookup table.

19. The method for acquiring an image of an object as claimed in claim 14, and wherein the beam of electromagnetic radiation is a beam of x-ray radiation.

* * * * *